(12) United States Patent
Almond et al.

(10) Patent No.: US 7,659,106 B2
(45) Date of Patent: Feb. 9, 2010

(54) NON-HOMOGENEOUS SYSTEMS FOR THE RESOLUTION OF ENANTIOMERIC MIXTURES

(75) Inventors: Merrick R. Almond, Apex, NC (US); Wang Yi Fong, Lexington, MA (US); Yao Yiming, Newton, MA (US)

(73) Assignees: Altus Pharmaceuticals Inc., Cambridge, MA (US); Gilead Sciences, Inc., Foster City, CA (US)

( * ) Notice: Subject to any disclaimer, the term of this patent is extended or adjusted under 35 U.S.C. 154(b) by 284 days.

(21) Appl. No.: 11/318,650

(22) Filed: Dec. 27, 2005

(65) Prior Publication Data

US 2007/0004024 A1    Jan. 4, 2007

Related U.S. Application Data

(63) Continuation of application No. 09/585,166, filed on Jun. 1, 2000, now Pat. No. 6,979,561, which is a continuation of application No. PCT/US99/23405, filed on Oct. 8, 1999.

(60) Provisional application No. 60/103,804, filed on Oct. 9, 1998.

(51) Int. Cl.
*C12P 41/00* (2006.01)
(52) U.S. Cl. ............... 435/280; 435/118; 435/135
(58) Field of Classification Search ........... 435/280, 435/118, 135
See application file for complete search history.

(56) References Cited

U.S. PATENT DOCUMENTS

| | | |
|---|---|---|
| 4,800,162 A | 1/1989 | Matson |
| 5,041,449 A | 8/1991 | Belleau et al. |
| 5,047,407 A | 9/1991 | Belleau et al. |
| 5,057,427 A | 10/1991 | Wald et al. |
| 5,204,466 A | 4/1993 | Liotta et al. |
| 5,210,085 A | 5/1993 | Liotta et al. |
| 5,248,776 A | 9/1993 | Chu et al. |
| 5,276,151 A | 1/1994 | Liotta |
| 5,466,806 A | 11/1995 | Belleau et al. |
| 5,486,520 A | 1/1996 | Belleau et al. |
| 5,538,975 A | 7/1996 | Dionne |
| 5,539,116 A | 7/1996 | Liotta et al. |
| 5,587,480 A | 12/1996 | Belleau et al. |
| 5,618,820 A | 4/1997 | Dionne |
| 5,663,320 A | 9/1997 | Mansour et al. |
| 5,684,164 A | 11/1997 | Belleau et al. |
| 5,693,787 A | 12/1997 | Mansour et al. |
| 5,696,254 A | 12/1997 | Mansour et al. |
| 5,700,937 A | 12/1997 | Liotta et al. |
| 5,728,575 A | 3/1998 | Liotta et al. |
| 5,744,596 A | 4/1998 | Mansour et al. |
| 5,756,706 A | 5/1998 | Mansour et al. |
| 5,763,606 A | 6/1998 | Mansour et al. |
| 5,814,639 A | 9/1998 | Liotta et al. |
| 5,827,727 A | 10/1998 | Liotta et al. |
| 5,892,025 A | 4/1999 | Liotta et al. |
| 5,914,331 A | 6/1999 | Liotta et al. |
| 5,914,400 A | 6/1999 | Liotta et al. |
| 5,922,867 A | 7/1999 | Mansour et al. |
| 6,979,561 B1 | 12/2005 | Almond et al. |

FOREIGN PATENT DOCUMENTS

| | | |
|---|---|---|
| EP | 0 337 713 A2 | 10/1989 |
| EP | 0 382 526 A2 | 8/1990 |
| EP | 0 515 144 A1 | 11/1992 |
| EP | 0 515 156 A1 | 11/1992 |
| EP | 0 526 253 A1 | 2/1993 |
| EP | 0 711 771 A2 | 5/1996 |
| EP | 0 513 200 B1 | 9/1998 |
| EP | 0 872 237 A1 | 10/1998 |
| JP | 08092269 A | 4/1996 |
| WO | WO 91/11186 A1 | 8/1991 |
| WO | WO 91/17159 A1 | 11/1991 |
| WO | WO 92/02617 A1 | 2/1992 |
| WO | WO 92/14743 A2 | 9/1992 |
| WO | WO 92/15308 A1 | 9/1992 |
| WO | WO 92/15309 A1 | 9/1992 |
| WO | WO 92/18517 A1 | 10/1992 |
| WO | WO 94/09793 A1 | 5/1994 |
| WO | WO 96/30369 A1 | 10/1996 |
| WO | WO 97/44445 A1 | 11/1997 |
| WO | WO 98/46732 A1 | 10/1998 |
| WO | WO 00/22157 A1 | 4/2000 |

OTHER PUBLICATIONS

Ariente-Fliche et al., "How to Synthesize Easily Dimethyl (2R) and (2S)-Formylcyclopropane-1,1-Dicarboxylate, a Precursor of a Wide Variety of Substituted Aminocyclopropanecarboxilic Acids," *Synth. Commun.*, 22(8):1149-1153 (1992).

(Continued)

*Primary Examiner*—Sandra Saucier
*Assistant Examiner*—Susan Hanley
(74) *Attorney, Agent, or Firm*—King & Spalding

(57) ABSTRACT

The present invention relates to a process for the biocatalyst-mediated enantioselective conversion of enantiomeric mixtures of hydrophobic esters using a biphasic solvent system. More particularly, the present invention relates to the enzyme-mediated enantioselective synthesis of anti-viral compounds, such as 2-hydroxymethyl-5-(5-fluorocytosin-1-yl)-1,3-oxathiolane (FTC) and its analogues, in a non-homogenous reaction system.

26 Claims, 1 Drawing Sheet

OTHER PUBLICATIONS

Basavaiah et al., "Enantioselective Synthesis of (1R,2R)- and (1S,2S)-2-Nitroxycyclohexan-l-ols," *Tetrahedron: Asymmetry*, 7(1):13-16 (1996,).

Basavaiah et al., "Enantioselective synthesis using crude enzymes," *Pure and Appl. Chem.*, 64(8):1067-1072 (1992).

Belleau, et al., "Oxidative Degradation of L-Ascorbic Acid Acetals to 2',3'-Dideoxy-3'-Oxaribofuranoside. Synthesis of Enantiomerically Pure 2',3'-Dideoxy-3'-Oxacytidine Stereoisomers as Potential Antiviral Agents," *Tet. Lett.*, 33(46):6949-6952 (1992).

Brand, S., et al., "New enantioselective routes to cyclic and acyclic S,O-acetals; enzymic resolution of .alpha.-acetoxysulfides:and enantiolselective synthesis of the antiviral agent Lamivudine," *Phosphorus, Sulfur, and Silicon and the Related Elements*, vol. 120-121, pp. 367-368 (1997).

Choi, W.-B., et al., "In situ complexation directs the stereochemistry of N-glycosylation in the synthesis of oxathiolanyl and dioxolanyl nucleoside analogues," *J. Am. Chem. Soc.*, 113(24):9377-9379 (1991).

Davies et al., "Biotransformations in Preparative Organic Chemistry. The Use of Isolated Enzymes and Whole Cell Systems in Synthesis," Academic Press: London, 1989, pp. 10, 25, 37, 43, 50, 76.

Drauz, K., and Waldmann, H., *Enzyme Catalysis in Organic Synthesis*, vol. 1, (VCH, Weinheim, Germany, 1995), pp. 23, 201, 202.

Du et al., "Asymmetric Synthesis of Oxazolidine Nucleosides and Related Chemistry," *Nucleosides and Nucleotides*, 17(1-3):1-13 (1998).

Hoong, L.K., et al, "Enzyme-Mediated Enantioselective Preparation of Pure Enantiomers of the Antiviral Agent 2',3'-Dideoxy-5-fluoro-3'-thiacytidine (FTC) and Related Compounds," *J. Org. Chem.*, 57:5563-5565 (1992).

Hultin et al., "Dilemma Regarding an Active Site Model for Porcine Pancreatic Lipase," *Tetrahedron Letters*, 33(11):1399-1402 (1992).

Jones, "Enzymes in Organic Synthesis," *Tetrahedron*, 42(13):3351-3403 (1986).

Jones, "Probing the specificity of synthetically useful enzymes," *Can. J. Chem.*, 71:1273-1282 (1993).

Kraus et al., "Synthesis of New 2,5-Substituted 1,3-Oxathiolanes. Intermediates in Nucleoside Chemistry," *Synthesis*, Nov. 1991:1046-1048.

Lalonde et al., "Cross-Linked Crystals of *Candida rugosa* Lipase: Highly Efficient Catalysts for the Resolution of Chiral Esters," *J. Am. Chem. Soc.*, 117(26):6845-6852 (1995).

Mahmoudian et al., "Resolution of 4-amino-cyclopentanecarboxylic acid methyl esters using hydrolytic enzymes," *Enzyme and Microbial Technology*, 14:911-916 (1992).

McIntosh et al., "2 Mercaptoaldehyde dimers and 2,5-dihydrothiophenes from 1,3-oxathiolan-5-ones," *Can. J. Chem.*, 61:1872-1875 (1983).

Milton et al., "Enzymatic Resolution of .alpha.-Acetoxysulfides: A New Approach to the Synthesis of Homochiral S,O-Acetals," *Tetrahedron: Asymmetry*, 6(8):1903-1906 (1995).

Norbeck, D.W. et al., "A new 2',3'-dideoxynucleoside prototype with in vitro activity against HIV," *Tetrahedron Letters*, 30(46):6263-6266 (1989).

Ohno et al., "Chiral Synthons by Ester Hydrolysis Catalyzed by Pig Liver Esterase," *Organic Reactions*, 37:1-55 (1989).

Provencher et al., "A Concluding Specification of the Dimensions of the Active Site Model of Pig Liver Esterase," *J. Org. Chem.*, 59:2729-2732 (1994).

Provencher et al., "Enzymes in Organic Synthesis 51. Probing the Dimensions of the Large Hydrophobic Pocket of the Active Site of Pig Liver Esterase," *Tetrahedron: Asymmetry*, 4(9):2025-2040 (1993).

Ross, A.C., et al., "Organic solvent functional group effect on enzyme inactivation by the interfactial mechanism," *J. Molec. Catalysis B. Enzymatic*, 8:183-192 (2000).

Schinazi et al., "Selective Inhibition of Human Immunodeficiency Viruses by Racemates and Enantiomers of cis-5-Fluoro-1-[2-(Hydroxymethyl)-1,3-Oxathiolan-5-yl]Cytosine," Antimicrobial Agents and Chemotherapy, 36(11):2423-2431 (1992).

Sih et al., "Resolution of Enantiomers via Biocatalysis," *Topics in Stereochemistry*, 1989:63-125.

Toone et al., "Active-Site Model for Interpreting and Predicting the Specificity of Pig Liver Esterase," *J. Am. Chem. Soc.*, 112:4946-4952 (1990).

Toone et al., "Enzymes in Organic Synthesis 49. Resolution of Racemic Monocyclic Esters with Pig Liver Esterase," *Tetrahedron: Asymmetry*, 2(3):207-222 (1991).

Toone et al., "Enzymes in Organic Synthesis 50. Probing the Dimensions of the Large Hydrophobic Binding Region of the Active Site of Pig Liver Esterase Using Substituted Aryl Malonate Substrates," *Tetrahedron: Asymmetry*, 2(10):1041-1052 (1991).

Whitesides et al., "Enzymes as Catalyst in Synthetic Organic Chemistry," *Angew. Chem. Int. Ed. Eng.*, 24(8):617-653 (1985).

NON-HOMOGENEOUS SYSTEMS FOR THE RESOLUTION OF ENANTIOMERIC MIXTURES

This application is a continuation of U.S. application Ser. No. 09/585,166, now U.S. Pat. No. 6,979,561, filed Jun. 1, 2000, which is a continuation of International Application No. PCT/US99/23405, filed Oct. 8, 1999, designating the United States, which claims priority to U.S. Provisional Application No. 60/103,804, filed Oct. 9, 1998.

TECHNICAL FIELD OF THE INVENTION

The present invention relates to a process for the biocatalyst-mediated enantioselective conversion of enantiomeric mixtures of hydrophobic esters using a biphasic solvent system. More particularly, the present invention relates to the enzyme-mediated enantioselective synthesis of anti-viral compounds, such as 2-hydroxymethyl-5-(5-fluorocytosin-1-yl)-1,3-oxathiolane (FTC) and its analogues, in a non-homogenous reaction system.

BACKGROUND OF THE INVENTION

Serious obstacles to commercially viable processes for the enzymatic resolution of enantiomeric mixtures of hydrophobic esters exist. For example, when using an enzymatic conversion process in the presence of an organic solvent, the rate of enzyme inactivation is very high relative to the same process performed in an aqueous solvent. A confounding problem is that solvents which are less destructive to the catalyst are often less able to solubilize the more hydrophobic substrates. Ideally, many processes would be more efficient if they were performed in more hydrophobic solvents, such as non-miscible organic solvents. One goal of the present invention is to provide a non-homogenous system, which allows higher concentrations of hydrophobic substrates to be converted to product, while simultaneously consuming less catalyst.

The above-cited obstacles must be overcome in order to reduce the cost of producing enantiomeric drugs anti-viral drugs. Such drugs are vital towards winning the struggle to conquering emerging viral diseases. For example, even today, the rate of HIV infection continues at a staggering pace, with 16,000 new infections per day worldwide [Balter, M. Science 280, 1863-1864 (1998)]. There are areas of sub-Saharan Africa where at least 25% of the population are infected, for example in Botswana and Zimbabwe. The cost of anti-viral drugs, however, is currently far beyond the reach of most such victims of HIV infection.

Nucleoside analogues, such as 3'-thiaribofuranonsyl-βL-cytosine ("3-TC"), 3'-azido-3'-deoxythymidine (AZT) [Blair E., Darby, G., Gough, E., Littler, D., Rowlands, D., Tisdale, M. *Antiviral Therapy*, BIOS Scientific Publishers Limited, 1998], (−)-2',3'-dideoxy-5-fluoro-3'-thiacytidine ("FTC") and 2',3'-dideoxy-3'-thiacytidine are important antiviral agents [Liotta, D. C. 216$^{th}$ ACS National Meeting, Medicinal Chemistry Abstract, Boston, Mass., Aug. 2327, 1998; Hoong, L. K., Strange, L. E., Liotta, D. C., Koszalka, G. W., Burns, C. L., and Schinazi, R. F., *J. Org. Chem.* 1992, 57, 5563-5565]. 3-TC has been marketed as both an anti-HIV and an anti-HBV drug and FTC is under clinical trial for evaluation as an anti-viral drug [Liotta, D. C., Schinazi, R. F., and Choi, W.-B., U.S. Pat. Nos. 5,210,085, 5,700,937 and 5,814,639]. Since it is the (−) enantiomer of both (−)-FTC and (−)-2',3'-dideoxy-3'-thiacytidine, which exhibits the most potent anti-viral activity and the least toxicity, as compared to the corresponding (+)-isomers, there is a pressing need for efficient cost-effective methods of preparation of both the (−)-FTC and (−)-2',3'-dideoxy-3'-thiacytidine isomers to expand treatment options of patients throughout the world [Liotta, D. C. 216$^{th}$ ACS National Meeting, Medicinal Chemistry Abstract, Boston, Mass., Aug. 23-27, 1998, Hoong, L. K., Strange, L. E., Liotta, D. C., Koszalka, G. W., Burns, C. L., and Schinazi, R. F., *J. Org. Chem.* 1992, 57, 5563-5565].

Many hydrolase enzymes have been used for the resolution of FTC esters [Hoong, L. K., Strange, L. E., Liotta, D. C., Koszalka, G. W., Burns, C. L., and Schinazi, R. F., *J. Org. Chem.* 1992, 57, 5563-5565]. Impediments remain, however, to developing practical enzyme mediated chemical processes for the production of FTC and similar compounds. First, the solubility of many FTC esters in aqueous media is too low to achieve economically viable production of resolved product. One possible solution has been to add a water miscible co-organic solvent to increase the concentration of the ester in solution. An example is the use of solutions of acetonitrile and water [Hoong, L. K., Strange, L. E., Liotta, D. C., Koszalka, G. W., Burns, C. L., and Schinazi, R. F., J. Org. Chem. 1992, 57, 5563-5565; Liotta et al., U.S. Pat. No. 5,827,727]. Although the use of a water miscible organic solvent and water solution increases the concentration of substrate in solution, it has the unfortunate effect of drastically lowering the enzyme catalyzed conversion and enzyme stability. This problem is especially pronounced, where the substrate is not completely dissolved, but is also present as an undissolved solid suspension (high concentration of substrate loading). Similar results were obtained in our laboratory. When water miscible organic solvents, such as isopropanol, dimethylformamide (DMF), 1-methyl-2-pyrrolidinone, dimethylsulfoxide (DMSO), methanol, acetonitrile, ethanol, 1-propanol were used as co-solvent for the resolution, the maximal substrate concentration loading was 3%. The presence of undissolved substrate decreased the enantioselectivity when the substrate concentration was beyond 3%. Furthermore, use of a water miscible organic solvent and water solution, at concentrations of water miscible organic co-solvents of greater than 20%, had a pronounced negative impact on enzyme activity, especially for porcine liver esterase (PLE).

The present invention specifically addresses several obstacles in the art that had the effect of making enzymatic resolution of enantiomeric mixtures uneconomical. First, it was thought that enzymatic conversion should be performed under homogenous conditions, because biphasic systems result in poor reproducibility [See Liotta et al., U.S. Pat. Nos. 5,827,727, 5,892,025, 5,914,331]. One potential advantage for the use of non-homogenous systems would be in enhanced solubilization of the substrate. Presumably, in a non-homogenous system, a higher concentration of many hydrophobic substrates could be accommodated. Prior to the present invention, it was believed that alcohol solvents should be avoided, because these solvents denature enzymes [Liotta et al., U.S. Pat. Nos. 5,827,727, 5,892,025, 5,914,331]. The present invention is an advance over the art because it specifically provides for the use of alcohol solvents which form non-homogenous systems with water. In addition, the use of non-homogenous solvent systems provides increased solubilization of more hydrophobic substrates than could be accommodated previously in the art. Furthermore, the present invention discloses a process which requires less enzyme per unit of product.

Additional improvements achieved via the present invention permit the use of several alcohol solvents in an enzymatic process. In addition, the present invention provides an alternative process mode, wherein enzyme and organic solvent requirements are further reduced by the addition of surfactants. Finally, the present invention is directed to providing a more efficient enzymatic process which maintains the enantioselectivity at a high level.

SUMMARY OF THE INVENTION

Figure 1:
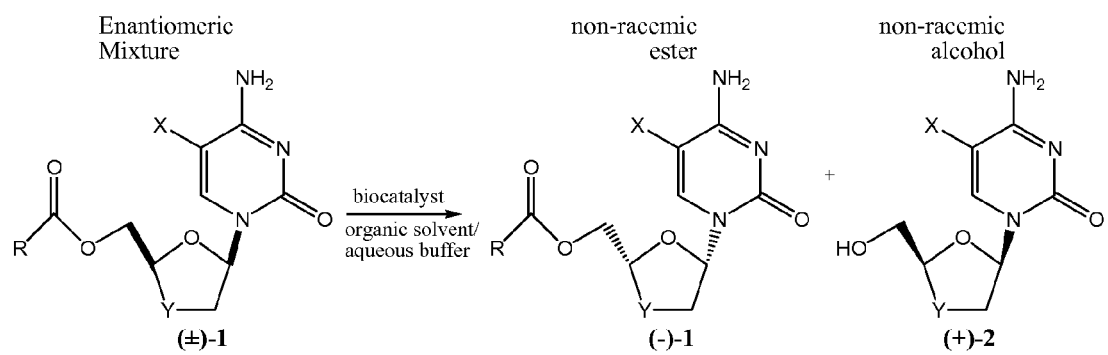
FIG. 1 depicts the enantioselective conversion of one enantiomeric form of an enantiomeric mixture of FTC butyrate to the corresponding non-racemic alcohol and the desired non-racemic ester.

The present invention is directed to several improvements in processes for producing a chiral, non-racemic ester. More specifically, the present invention is directed to providing an improved process that uses a biphasic non-homogenous system employing biocatalysts to resolve enantiomeric mixtures of FTC esters and analogues of FTC esters. The invention is further directed to improvements which allow high substrate loading and consume reduced amounts of enzyme.

A first improved process according to this invention provides for dispersing an enantiomeric mixture of an ester in an organic solvent system to produce an organic component at a high substrate loading. An aqueous component is provided and preferentially contains a dispersed hydrolase enzyme. Alternatively, the hydrolase enzyme can be added to the entire non-homogenous system or less preferentially to the organic component. The process further requires contacting the organic component and the aqueous component to form a non-homogenous system, under conditions which permit the resolution of the mixture to produce a chiral non-racemic ester and a non-racemic alcohol. The combination of the organic component and aqueous component form a non-homogenous system. By using a non-homogenous system, much higher substrate concentrations are possible. In one embodiment, after the reaction is carried out, the chiral non-racemic ester compound may be isolated from the organic component and the chiral non-racemic alcohol compound may be isolated from the aqueous component. The isolation steps may vary, depending on the particular compound and conditions.

This invention also provides an alternative process that produces improved results by drastically reducing the amount of enzyme required for producing a given product. Such improvement is achieved by the addition of surfactant to said non-homogenous system, to produce an improved non-homogenous system that requires less organic solvent to solubilize the substrate.

In another embodiment, the invention provides a process using a lowered organic/water phase ratio, which results in a further reduction in the required hydrolase enzyme.

In another embodiment of this invention, addition of surfactant to the system permits enhancement of enzyme reaction rates and better solubilization of substrate. Higher rates of reaction result in a lower overall enzyme costs for operating the process.

DETAILED DESCRIPTION OF THE INVENTION

In the following description, terms are defined as follows:
Biocatalyst—a protein molecule, such as a hydrolase enzyme. Examples include esterases, proteases and lipases.
Chiral compound—a compound that is not superposable on its mirror image, and usually contains an asymmetric carbon atom, where four different groups are attached to the same carbon.

Co-solvent—an organic solvent.
Conversion—the process of treating an enantiomeric mixture of compounds with a catalyst which transforms a single enantiomer into a different chemical entity.
Diastereomers—stereoisomers that are not related as mirror reflections of one another.
Dispersing—distributing the enzyme or enantiomeric mixture material in the solvent. The enzyme may be in the form of a crosslinked enzyme crystal, immobilized enzyme, or soluble enzyme, and the enantiomeric mixture may be soluble or contain residual particulates. The disperse system may contain up to three phases with solid crystalline and/or particulate materials and two different liquid phases.
Enantiomers—pairs of stereoisomers that are mirror reflections of each other. An enantiomer is non-superposable on its mirror image. Enantiomers are chiral stereoisomers that differ only in how they react with other chiral molecules and in their behavior toward plane polarized light. Separate enantiomers rotate the plane of polarized light in equal but opposite directions. Different enantiomers are distinguished by the R and S designations and whether the plane of polarized light is rotated to the right (dextrorotary (+)) or to the left (levorotatory (−)).
Enantiomeric excess—in a mixture (solution) of two enantiomers where one enantiomer is present to a greater extent, the solution will display optical rotation (+ or − rotation) corresponding to the enantiomer which is present in excess. Enantiomeric excess is the percentage of the enantiomer found in excess over that of the racemic mixture and is calculated as follows:

(specific rotation of the mixture)÷(specific rotation of the pure enantiomer)×100=% enantiomer excess.

Enantiomeric mixture—a mixture of two enantiomers.
Enantioselectivity—a preference for converting one enantiomer from an enantiomeric mixture.
FTC butyrate—refers to an enantiomeric mixture of the compound 2',3'-dideoxy-5'-butyrate-5-fluoro-3'-thiacytidine or, using alternative nomenclature, the compound is 2-butyryloxymethyl-5-(5-fluorocytosin-1-yl)-1,3-oxathiolane or, less formally the 5' butyrate ester of 2-hydroxymethyl-5-(5-fluorocytosin-1-yl)-1,3-oxathiolane.
Incompletely water-miscible organic solvent—an organic solvent which is not fully soluble in water at 25° C. and forms non-homogenous solutions with water. not completely.
Non-homogenous system—a biphasic medium comprising a biocatalyst, organic component, aqueous component and a substrate. A non-homogenous system may also be referred to as a non-homogenous medium or a non-homogenous condition or a non-homogenous composition.
Organic solvent system—a solution comprising one or more of the following solvents: $C_1$-$C_8$ unsubstituted alkanes, alcohols, aromatics, ketone ethers, nitro, halo-alkane or -aromatic organic solvent, such as tert-amyl alcohol, iso-amyl alcohol, 1-pentanol, 3-pentanol, 1-butanol, 2-butanol, tert-butanol, 3-methyl-3-pentanol, 4-methyl-2-pentanol, 3-ethyl-3-pentanol, 3-heptanol, toluene, butylacetate, nitroethane, nitromethane, dichloromethane, methyl isobutyl ketone, dimethyl sulfide, sulfolane or any other not more than about 50% water miscible organic solvent which facilitates the dissolution of an enantiomeric mixture without destroying the enzyme's ability to function.
Racemic mixture—an equimolar mixture of two enantiomers, also known as a racemic modification, usually produced as a result of a chemical reaction at a chiral center where neither enantiomeric product is preferred.

Resolving enantiomers or resolution—the process of separating pairs of enantiomers from an enantiomeric mixture.

Resolution of a racemic mixture—the separation of a racemic mixture of enantiomers.

Stereochemistry of FTC and FTC Butyrate—The stereochemistry of the FTC compounds referred to throughout this application are shown below:

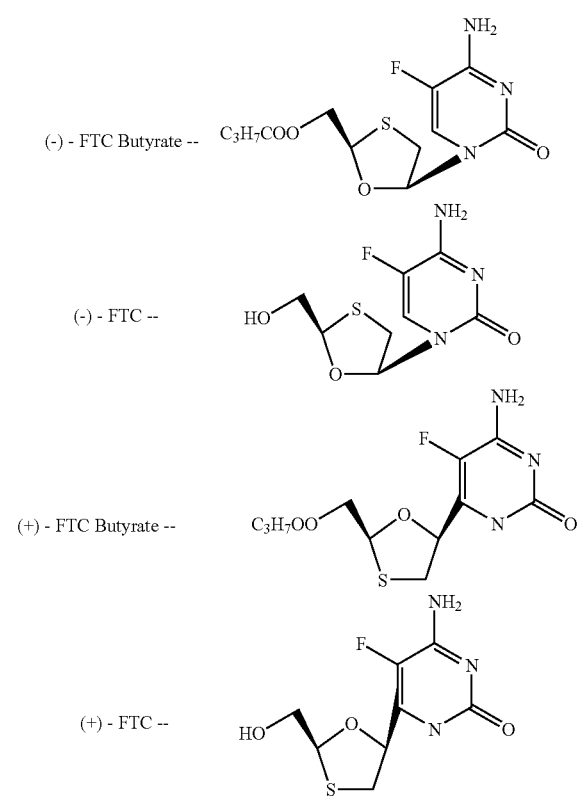

Stereoisomer—a compound whose constituent atoms are arranged in the same order as that of another compound, but differ only in the arrangement of their atoms in space. Examples of stereoisomers are enantiomers and diastereomers.

Substrate loading—the concentration of an enantiomeric mixture. For the examples shown below, substrate loading is expressed as % (weight/volume of the non-homogenous system), i.e., based on total solvent volume. To reiterate, percentage (%) (weight/volume) substrate loading is based on the volume of the entire non-homogenous system, which includes both the aqueous and organic components.

Surfactant—surface active agents that reduce the surface tension of solutions when dissolved in said solutions. Surfactants also reduce the interfacial tension between two liquids, or between a liquid and a solid. Surfactants belong to three categories which function through a similar mechanism. Those categories include detergents, emulsifiers and wetting agents depending on the nature of the surfaces involved. The surfactant concentration is expressed as percentage (%) (weight/volume) and is based on the volume of the entire non-homogenous system, which includes both the aqueous and organic components.

Water-immiscible organic solvent—an organic solvent which has a maximum solubility in water of 10% at 25° C. and forms non-homogenous solutions with water. The organic solvent concentration is expressed as percentage (%) (volume/volume) and is based on the volume of the entire non-homogenous system, which includes both the aqueous and organic components.

Not more than about 50% water-miscible organic solvent—an organic solvent which is not more than about 50% soluble in water at 25° C. and forms a non-homogenous solution with water.

Water-miscible organic co-solvent—an organic solvent which is fully miscible in water at 25° C.

The present invention provides a process for producing a chiral, non-racemic ester of Formula I using a hydrolase enzyme:

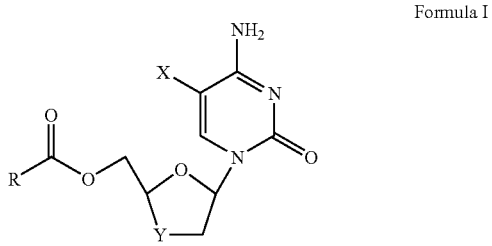

Formula I wherein:
R is $C_1$-$C_8$ alkyl, alkenyl, or alkynyl;
X=H, or F;
Y=$CH_2$, O, S, Se, or NH;
said process comprising the steps of:
(a) dispersing an enantiomeric mixture of an ester of Formula I at a concentration of between about 1 and about 25% (weight/volume of the non-homogenous system), in an organic solvent system to produce an organic component;
(b) providing an aqueous solvent system to produce an aqueous component; and
(c) contacting said organic component and said aqueous component to form a non-homogenous system, under conditions which permit the resolution of the mixture to produce a chiral non-racemic ester of Formula I and a non-racemic alcohol of Formula II;

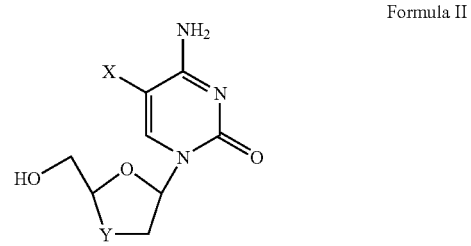

Formula II wherein:
X=H, or F;
Y=$CH_2$, O, S, Se, or NH, and
wherein said hydrolase enzyme is dispersed in either said organic component, said aqueous component or said non-homogenous system.

The present invention also provides a process for producing a chiral, non-racemic hydrophobic ester using a hydrolase enzyme, said process comprising the steps of:
(a) dispersing an enantiomeric mixture of said hydrophobic ester at a concentration of between about 1 and about 25% (weight/volume of the non-homogenous system), in an organic solvent system to produce an organic component;
(b) providing an aqueous solvent system to produce an aqueous component; and
(c) contacting said organic component and said aqueous component to form a non-homogenous system, under conditions which permit the enantioselective conversion of one enantiomeric form of said enantiomeric mixture to the corresponding alcohol; and
wherein said hydrolase enzyme is dispersed in either said organic component, said aqueous component or said non-homogenous system.

Alternatively, the present invention provides processes for producing a chiral, non-racemic ester of Formula I from an enantiomeric mixture of formula I or from an enantiomeric mixture of a hydrophobic ester, wherein said process further comprises a surfactant.

In addition, the present invention provides a process for producing a chiral, non-racemic ester of 2-butyryloxymethyl-5-(5-fluorocytosin-1-yl)-1,3-oxathiolane using a hydrolase enzyme, said process comprising the steps of:
(a) dispersing an enantiomeric mixture of said 2-butyryloxymethyl-5-(5-fluorocytosin-1-yl)-1,3-oxathiolane at a concentration of between about 1 and about 25% (weight/volume of the non-homogenous system), in an organic solvent system to produce an organic component;
(b) providing an aqueous solvent system to produce an aqueous component; and
(c) contacting said organic component and said aqueous component to form a non-homogenous system, under conditions which permit the enantioselective conversion of one enantiomeric form of said enantiomeric mixture to the corresponding alcohol;
wherein said hydrolase enzyme is dispersed in either said organic component, said aqueous component or said non-homogenous system; and
wherein the concentration of said enantiomeric mixture is calculated based on the volume of said non-homogenous system.

One embodiment of this invention provides a process for producing a chiral, non-racemic ester of 2-butyryloxymethyl-5-(5-fluorocytosin-1-yl)-1,3-oxathiolane using a hydrolase enzyme, said process comprising the steps of:
(a) dispersing an enantiomeric mixture of said 2-butyryloxymethyl-5-(5-fluorocytosin-1-yl)-1,3-oxathiolane at a concentration of between about 1 and about 25% (weight/volume of the non-homogenous system), in an organic solvent system to produce an organic component;
(b) providing an aqueous solvent system to produce an aqueous component; and
(c) contacting said organic component and said aqueous component to form a non-homogenous system, under conditions which permit the enantioselective conversion of one enantiomeric form of said enantiomeric mixture to the corresponding alcohol;
wherein said hydrolase enzyme is dispersed in either said organic component, said aqueous component or said non-homogenous system;
wherein said organic component comprises between about 5 and about 90% of said non-homogenous system;
wherein said non-homogenous system also comprises between about 1 and about 20% of surfactant; and
wherein said surfactant concentration is calculated based on the volume of said non-homogenous system.

Another object of the present invention is to provide a non-homogenous system for producing a chiral, non-racemic hydrophobic ester using a hydrolase enzyme, comprising:
(a) a hydrolase enzyme;
(b) a hydrophobic ester substrate;
(c) an organic component; and
(d) an aqueous component.

It is an object of this invention to provide a process for resolving a desired enantiomer from an enantiomeric mixture.

It is also an object of this invention to provide a process for resolving a desired enantiomer from an enantiomeric mixture of hydrophobic esters.

It is a further object of this invention to provide a process for resolving enantiomers of anti-viral compounds having Formula I above.

The most preferred embodiment of this invention provides a process for resolving enantiomeric FTC butyrate (or where R is propyl, X=F and Y=S of compound Formula I above).

Substrate loading entails dispersing an enantiomeric mixture of a hydrophobic ester in an organic solvent system to produce an organic component. The concentration range expressed in units of % (weight/volume of the non-homogenous system) is selected from the group consisting of ranges between about 0.5% and about 45%; between about 1.0% and about 45%; between about 5.0% and about 45%; between about 10% and about 40%; between about 10% and about 30%; between about 5 and about 20%; between about 1% and about 5%; and between about 10% and about 20%.

In a preferred embodiment, the organic solvent systems of this invention, comprise one or more, not more than about 50% water miscible organic solvents, that facilitate dissolution of the enantiomeric mixture.

In the next preferred embodiment, the organic solvent systems of this invention, comprise one or more $C_4$-$C_8$ alcohols.

In the most preferred embodiment, the organic solvent systems of this invention, comprise one or both of n-amyl alcohol or 3-methyl-3-pentanol.

In a preferred embodiment, the aqueous solvent systems of this invention comprise water, one or more buffering salts, alkalizing agents, antimicrobial preservatives, stabilizers, filtering aids, co-enzymes, or other excipients that facilitate dispersion and function of the enzyme.

In the next preferred embodiment, the aqueous solvent systems of this invention comprise water, one or more buffering salts, alkalizing agents, or other excipients that facilitate dispersion and function of the enzyme.

In a next preferred embodiment, the aqueous solvent systems of this invention comprise water, and between about 0.01 and about 0.5 molar phosphate buffer at a pH of between about 7.0 and about 8.0.

In the most preferred embodiment, the aqueous solvent systems of this invention comprise water, between about 0.2 and about 0.4 molar phosphate buffer at a pH of between about 7.2 and about 7.8.

In another embodiment of this invention, the hydrolase enzyme is capable of resolving a pair of enantiomers.

In another embodiment of this invention, the hydrolase enzyme is capable of resolving a pair of enantiomers by an enzyme catalyzed stereoselective reaction with one enantiomer.

In a preferred embodiment of this invention, the hydrolase enzyme is capable of resolving a pair of enantiomers by an enzyme catalyzed stereoselective conversion of one enantiomer.

In the most preferred embodiment of this invention, the hydrolase enzyme is capable of resolving a pair of enantiomers by the enzyme catalyzed stereoselective conversion of the (+) enantiomer of 2-butyryloxymethyl-5-(5-fluorocytosin-1-yl)-1,3-oxathiolane (or where R is propyl, X=F and Y=S of Formula I above or FTC butyrate).

In one embodiment of this invention, the biocatalyst is an enzyme.

In another preferred embodiment of this invention, the enzyme is a hydrolase.

In a preferred embodiment of this invention, the enzyme is selected from the group consisting of esterases, lipases and proteases.

In the most preferred embodiment of this invention, the enzyme is selected from the group consisting of porcine pancreatic lipase ("PL"), *Pseudomonas* species lipase, *Aspergillus niger* lipase, subtilisin, or porcine liver esterase ("PLE").

In one embodiment of this invention, the biocatalyst is added to the non-homogenous system after the aqueous component is contacted with the organic component to make a non-homogenous system.

In another embodiment of this invention, a biocatalyst is added to the organic phase as part of the organic component before the aqueous component is contacted with the organic component to make a non-homogenous system.

In a preferred embodiment of this invention, a biocatalyst is added to the aqueous phase to create an aqueous component after the aqueous component is contacted with the organic component but before agitation and mixing to make a non-homogenous system.

In the most preferred embodiment of this invention, a biocatalyst is added to the aqueous phase to create an aqueous component before the aqueous component is contacted with the organic component to make a non-homogenous system.

In one embodiment of this invention, the non-homogenous system used in the process to resolve enantiomeric mixtures contains surfactant. The concentration range of surfactant in % (weight/volume of the non-homogenous system) is selected from the group consisting of between about 1 and about 30% of surfactant; between about 1% and about 20% of surfactant; between about 1% and about 10% of surfactant; between about 1% and about 5% of surfactant; between about 5% and about 30% of surfactant; between about 10% and about 25% of surfactant; between about 15% and about 25% of surfactant; between about 20% and about 30% of surfactant; and between about 5% and about 15% of surfactant.

In one embodiment of this invention, the enzyme is immobilized on a matrix.

In a preferred embodiment of this invention, the enzyme form is that of a crosslinked enzyme crystal, such as, for example, those described in PCT patent application WO 92/02617 (Navia et al.).

In the next preferred embodiment of this invention, the enzyme form is that of a controlled dissolution crosslinked protein crystal, such as, for example, those described in PCT patent application WO 98/46732 (Margolin et al.).

In the most preferred embodiment of this invention, the enzyme is in a soluble form.

In one embodiment of this invention, said non-homogenous systems comprise between about 10% and 99% organic component. In another embodiment of this invention, said non-homogenous systems comprise between about 10% and about 90% organic component. More preferably non-homogenous systems comprise between about 20% and about 80% organic component. Even more preferably, said non-homogenous systems comprise between about 30% and about 70% organic component. In an even more preferred embodiment, said non-homogenous systems comprise between about 10% and about 50% organic component. In another preferred embodiment, said non-homogenous systems comprise between about 10% and about 60% organic component. In a further preferred embodiment, said non-homogenous systems comprise between about 20% and about 70% organic component. In still another preferred embodiment, said non-homogenous systems comprise between about 50% and about 20% organic component.

In one embodiment of this invention, said processes for resolving a desired enantiomer are carried out at a temperature or temperatures selected from the group consisting of between about 0° C. and about 45° C.; between about 10° C. and about 45° C.; between about 20° C. and about 45° C.; between about 30° C. and about 45.degree° C.; between about 10° C. and about 40° C.; between about 10° C. and about 30° C.; between about 10° C. and about 25° C.; between about 15° C. and about 40° C.; between about 15° C. and about 35° C.; between about 15° C. and about 30° C.; between about 15° C. and about 25° C.; and between about 20° C. and about 35° C.

In a preferred embodiment, said aqueous component used in the processes of this invention comprises at least 10% (volume/volume) of said non-homogenous system.

In the next preferred embodiment, said aqueous component used in the processes of this invention comprises at least 50% (volume/volume) of said non-homogenous system.

In the most preferred embodiment, said aqueous component used in the processes of this invention comprises at least 90% (volume/volume) of said non-homogenous system. homogeneous In one embodiment of this invention, said process for resolving a desired enantiomer is carried out in a non-homogeneous system comprising a surfactant. When a surfactant is part of said non-homogeneous system, the concentration range of the organic component in % (volume/volume) is selected from the group consisting of between about 5% and about 90% of said non-homogeneous system; between about 5% and about 80% of said non-homogeneous system; between about 5% and about 70% of said non-homogeneous system; between about 5% and about 60% of said non-homogeneous system; between about 5% and about 50% of said non-homogeneous system; between about 5% and about 30% of said non-homogeneous system; between about 5% and about 20% of said non-homogeneous system; between about 5% and about 10% of said non-homogeneous system; between about 10% and about 30% of said non-homogeneous system; between about 10% and about 20% of said non-homogeneous system; between about 20% and about 70% of said non-homogeneous system; or between about 25% and about 50% of said non-homogeneous system; and between about 30% and about 60% of said non-homogeneous system.

The reaction scheme for resolution of an enantiomeric mixture is illustrated in the reaction shown in FIG. 1, where the substrates were either, acetate, formate, propionate, butyrate, pentanoate or other n-alkyl and branched chain or aryl esters of FTC, or derivatives of such esters of FTC and the organic co-solvents were any that were not more than about 50% water miscible alcoholic, alkane, aromatic, ketone ether, nitro, halo-alkane or aromatic organic solvents, such as n-amyl alcohol, iso-amyl alcohol, tert-amyl alcohol, 3-pentanol, 1- or 3-heptanol, 3-methyl-3-pentanol, 4-methyl-2-pentanol, 3-ethyl-3-pentanol, 1- or 2-butanol, nitromethane, dichloromethane, methyl isobutyl ketone, dimethyl sulfide, sulfolane, and others.

In FIG. 1, the products of the reaction were a non-racemic ester and a non-racemic alcohol (FIG. 1). In one example, when X is Fluorine, R is $C_3H_7$ and Y is Sulfur, then compound A represents an enantiomeric mixture of FTC butyrate. Various hydrolytic enzymes such as, porcine liver esterase (PLE), lipase from *Pseudomonas* species (PSL) and lipase from *Aspergillus niger* (ANL) have been used as catalyst [For PLE catalyzed reactions in mixed organic solvents: See Ariente-Fliche, C., Braun, J., and Le Goffic, F., *Synth. Commun.* 22, 1149-1153 (1992); Basavaiah, D., and Krishna, P. R., *Pure & Applied Chem.,* 64, 1067-1072 (1992); Basavaiah, D., Pandiaraju, S., and Muthukumaran, K., *Tetrahedron: Asymmetry,* 7, 13-16, (1996); Mahmoudian, M., Baines, B. S., Dawson, M. J., and Lawrence, G. C., Enzyme Microb. Technol., 14, 911-916, (1992); Izumi, T. and Kasahara, A., Japanese patent JP08092269A (1996)].

R is $C_1$-$C_8$ alkyl, alkenyl, or alkynyl; X=H, or F; Y=$CH_2$, O, S, Se, or NH; the biocatalyst can be either soluble enzyme, immobilized, or the cross-linked enzyme crystal form; the organic co-solvent can be any that were not more than about 50% water miscible organic solvents, such as n-amyl alcohol, iso-amyl alcohol, tert-amyl alcohol, 3-pentanol, 1- or 3-heptanol, 3-Me-3-pentanol, 4-Me-2-pentanol, 3-Et-3-pentanol, 1- or 2-butanol, nitromethane, dichloromethane and others.

The biocatalysts may be either soluble enzyme, immobilized enzyme or crosslinked crystal (CLEC™) form of the enzyme (Altus Biologics, Inc., Cambridge, Mass.). The reaction can be performed in a batch reactor, a column, a hollow-fiber membrane [Enzyme Catalysis in Organic Synthesis, pp. 138-150, edited by Drauz, K. and Waldmann, H., VCH Verlagsgesellschaft GmbH, Weinheim, 1995] or membrane reactor [Dodds, D. R., Lopez, J. L., Zepp, C. M., and Rossi, R. F. PCT Patent Application No. WO 90/04643. May, 1990].

The choice of which particular enzyme is best for a given substrate pair is determined by treating samples of the enantiomeric pairs with various enzymes such as porcine liver esterase, porcine pancreatic lipase, lipases from *Pseudomonas* species (PSL) and lipase from *Aspergillus niger* (ANL), and proteases such as subtilisin or α-chymotrypsin. After treatment of the enantiomeric mixture with the resolving enzyme, the products are isolated using standard extraction or chromatography procedures. The enzyme producing the greatest enantiomeric excess of the desired product should be the best candidate for use in the process.

The process can be further improved by choosing a given enantiomeric mixture and resolving enzyme combination and determining the ideal solvent conditions for the reaction. In a biphasic system, the choice of organic solvent must be determined. The optimum organic solvent can be determined by treating samples of the enantiomeric mixture with the selected enzyme in the presence of the same amount of an array of not more than about 50% water miscible organic solvents. Particular solvents include any not more than about 50% water miscible (solubility less than 50% in water at room temperature) alcoholic, alkane, aromatic, ketone ether, nitro, halo-alkane or aromatic organic solvents, such as n-amyl alcohol, iso-amyl alcohol, tert-amyl alcohol, 3-pentanol, 1- or 3-heptanol, 3-methyl-3-pentanol, 4-methyl-2-pentanol, 3-ethyl-3-pentanol, 1- or 2-butanol, nitromethane, dichloromethane, methyl isobutyl ketone, dimethyl sulfide, sulfolane, etc. Following treatment of an enantiomeric mixture with the resolving enzyme in the presence of equal amounts of various solvents, the products are isolated using standard extraction or chromatography procedures. The solvent/enzyme pair producing the greatest enantiomeric excess of the desired product should be the best candidate for use in the process.

The relative quantity of the selected organic solvent should also be evaluated in order to achieve the best results. To do this, a similar procedure as described above is followed. Using a particular enzyme/racemic mixture, the ratio of the selected organic solvent/aqueous solvent is varied in a manner such as the following: 95:5, 90:10, 80:20, 70:30, 60:40, 50:50, 40:60, 30:70, 20:80, 10:90 and 5:95, ([organic solvent]: [aqueous solvent]). Identical samples of an enantiomeric mixture are treated with a standard amount of a particular enzyme in the presence of varying ratios of organic solvent to aqueous solvent for a set time. The total volume is kept constant. Following treatment of an enantiomeric mixture with the resolving enzyme in the presence of equal amounts of various solvents, the products are isolated using standard extraction or chromatography procedures. The solvent system/enzyme pair producing the greatest enantiomeric excess of the desired product should be the best candidate for use in the process.

Alternatively, for some racemic mixture:enzyme:organic solvent combinations, enzyme activity may be enhanced and organic solvent levels reduced by adding surfactants to the reaction. In order to evaluate whether a surfactant should be added to a particular process. Some variation of the following process may be pursued. First, a surfactant is selected by treating samples of an enantiomeric mixture with the selected enzyme and an array of surfactants in the presence of a non-homogeneous system composed of a not more than about 50% water miscible organic solvent and an aqueous solvent. The system should be one which is compatible with carrying out the reaction in the absence of a surfactant. Examples of surfactants include the TVVEEN®s, (polyoxyethylenesorbitan), such as TWEEN® 20 (polyoxyethylenesorbitan monolaurate) TWEEN® 80, PRIONEX® (10% aqueous solution of a polypeptide fraction of porcine dermal collagen), TEEPOL® HB7 (alkyl ($C_9$-$C_{13}$) sodium sulfates), TERGITOL® TMN-6 (2,6,8, Trimethyl-4-nonyloxypolyethylenoxyethanol), TERGITOL® TMN-10 (2-(2,6,8-trimethylnonan-4-yloxy)ethanol), TERGITOL® NP-4 (nonylphenol ethoxylate), TERGITOL® 15-S-3 (secondary alcohol ethoxylate), IGEPAL® CA-630 (branched octylphenoxypoly(ethyleneoxy)ethanol), Tyloxapol (Phenol, 4-(1,1,3,3-tetramethylbutyl) polymer with formaldehyde and oxirane), Glucodeoxycholic acid, octyl β-gluco-pyranoside, Chaps (3-[(3-cholamidopropyl)dimethylammonio]-1-propanesulfonate), dioctyl sulfosuccinate, or deoxycholic acid. Following treatment of an enantiomeric mixture with the resolving enzyme in the presence of a biphasic solvent system and constant amount of various surfactants, the products are isolated using standard extraction or chromatography procedures. The solvent/enzyme/surfactant combination producing the greatest enantiomeric excess of the desired product in a set time should be the best candidate for use in the process.

The surfactant may be added at a concentration or range of concentrations depending on how many samples can be processed at one time. For a given solvent/enzyme/surfactant combination, the optimal surfactant concentration should be determined. One of skill in the art will appreciate that an array of independent reactions should be set up, differing only by the concentration of surfactant. For example, the reaction may be carried out using PLE in 20% pentanol and 80% Tris(hydroxymethyl)aminomethane or 2-amino-2-(hydroxymethyl)-1,3-propanediol buffer at pH 7.4. Ten identical reactions may be set up, having the following surfactant concentrations: 1%, 3%, 5%, 7.5%, 10%, 12.5%, 15%, 20%, 25% and 30%. Following treatment of an enantiomeric mixture with the resolving enzyme in the presence of a biphasic solvent system and increasing surfactant concentration for a set time, the products are isolated using standard extraction or chromatography procedures. The solvent/enzyme/surfactant combination producing the greatest enantiomeric excess of the desired product in a set time should be the best candidate for use in the process.

Surfactants useful for carrying out this invention include cationic, anionic, non-ionic or amphoteric, or mixtures thereof. The preferred surfactant will depend upon the particular enzyme substrate components. Such screening procedures are well known to those of skill in the art. Illustrative screening processes are set forth in Examples 14-30.

Examples of useful cationic surfactants include amines, amine salts, sulfonium, phosphonium and quarternary ammonium compounds. Specific examples of such cationic surfactants include:

Methyl trioctylammonium chloride
(Aliquat 336)
N,N',N'-polyoxyethylene(10)-N-tallow-1,3-diaminopropane
(EDT-20,' PEG-10 tallow).

Useful anionic surfactants include, for example, linear alkylbenzene sulphonate, alpha-olefin sulphonate, alkyl sulphate, alcohol ethoxy sulfate, carboxylic acids, sulfuric esters and alkane sulfonic acids. Examples of anionic surfactants include:

TRITON® QS-30 (Anionic octyl phenoxy polyethoxyethanol)
AEROSOL® 22 (Tetrasodium N-(1,2-dicarboxyethyl)-N-octadecyl sulfosuccinamate)
AEROSOL® OT (dioctyl sulfosuccinate)
Alkyl Sodium Sulfate (NIAPROOF®):
Type-4 (Sodium 7-ethyl-2-methyl-4-undecyl sulfate)
Type-8 (Sodium ethylhexyl sulfate)
Alkyl ($C_9$-$C_{13}$) Sodium Sulfates (TEEPOL HB7®)

Non-ionic surfactants useful for stabilization include nonyl phenol ethoxylate, alcohol ethoxylate, sorbitan trioleate, non-ionic block copolymer surfactants, polyethylene oxide or polyethylene oxide derivatives of phenol alcohols or fatty acids. Examples of non-ionic surfactants include:

Polyoxyethylene Ethers:
4 lauryl Ether (BRIJ® 30)
23 lauryl Ether (BRIJ® 35)
Octyl Phenoxy polyethoxyethanol (TRITON®):
Tx-15
Tx-100
Tx-114
Tx-405
DF-16
N-57
DF-12
CF-10
CF-54

Polyoxyethylenesorbitan:
Monolaurate (TWEEN® 20)

Sorbitan:
Sesquioleate (ARLACEL® 83)
Trioleate (SPAN® 85)

Polyglycol Ether, (TERGITOL®):
Type NP-4
Type NP-9
Type NP-35
Type TMN-10
Type 15-S-3
Type TMN-6 (2,6,8, Trimethyl-4-nonyloxypolyethylenoxyethanol)
Type 15-S-40.

After selecting a suitable surfactant, the ratio of organic solvent may sometimes be reduced significantly without losing product yield or enantioselectivity. One of skill in the art will appreciate that one such procedure for determining how much to lower the organic solvent is as follows: Using a particular enzyme/racemic mixture/surfactant combination the ratio of the selected organic solvent to aqueous solvent is varied as follows: [% organic solvent: % aqueous solvent], 95:5, 90:10, 80:20, 70:30, 60:40, 50:50, 40:60, 30:70, 20:80, 10:90 and 5:95, and other ratios as required. Samples of an enantiomeric mixture are treated with a standard amount of a particular enzyme in the presence of varying ratios of organic solvent to aqueous solvent and surfactant for a set time. Following treatment of an enantiomeric mixture with the resolving enzyme in the presence of equal amounts of various solvents, the products are isolated using standard extraction or chromatography procedures. The solvent/enzyme pair producing the greatest enantiomeric excess of the desired product should be the best candidate for use in the process.

An additional consideration for carrying out the process of the present invention is the cost of the enzyme per unit of product produced. The present invention is directed to reducing the enzyme requirements of the process on a per unit of product basis. In one embodiment, the amount of organic component is reduced in the non-homogeneous system. In another embodiment, a surfactant is added to the non-homogeneous system to further reduce the amount of enzyme required and further reduce the cost of operating the process.

The present invention is particularly directed to enzyme reactions wherein the substrate comprises a hydrophobic ester. The present invention is additionally directed to enzyme reactions wherein the substrate is relatively insoluble in aqueous solutions. The use of a non-homogeneous system having incompletely water miscible organic co-solvents provides improved salvation for hydrophobic esters and other hydrophobic and insoluble compounds as compared to systems using water miscible organic solvents.

In order that this invention may be better understood, the following examples are set forth. These examples are for the purpose of illustration only and are not to be construed as limiting the scope of the invention in any matter.

EXAMPLES

Example 1

Porcine Liver Eaterase Catalyzed Resolution of FTC Butyrate

Racemic FTC-butyrate (1.0 g) was dissolved in 5.0 ml of n-amyl alcohol by heating to 75° C. for 30 minutes to make an organic component. The organic component was then mixed with an aqueous component comprising 3.8 ml of 0.3 M pH 7.5 phosphate buffer and the non-homogeneous system was allowed to cool to 35° C. Porcine liver esterase solution, 1.2 ml of 650 U/ml Altus PLE solution (Altus Biologics, Cambridge, Mass.) was then added to the aqueous layer and the resulting suspension was stirred with gentle agitation. The temperature was maintained at 32° C. by an external water-bath. The pH was maintained at 7.5 by the addition of 50% aqueous sodium hydroxide as necessary. The optical purity of the unreacted (−)-butyrate ester and the (+)-FTC alcohol product were monitored by HPLC analysis using a chiral stationary phase column. After 24 hours, the (+)-enantiomer of the FTC ester was completely converted based on HPLC analysis as described below. Extraction of the unreacted ester from the organic phase and evaporation of the organic solvent gave the desired (−)-FTC ester. The recovered yield was 89.4% based on the single (−) enantiomer and the optical purity was greater than 99%.

Procedures

Chiral HPLC conditions: CHIRAPAK® AS; 0.46 cm×25 cm HPLC column (Daicel Chemical Inc.), mobile phase=100% acetonitrile, flow rate=1 ml/min., uv detection at 260 nm. Retention times: (−)-FTC butyrate, 6.2 min.; (−)-FTC, 7.4 min.; (+)-FTC butyrate, 8.8 min.; and (+)-FTC, 11.4 min.

Enzyme activity was determined by the conversion of ethyl butyrate using a Radiometer pH-stat apparatus to follow the production of acid. Ethyl butyrate (40 ml) was added to 20 ml of 5 mM boric acid (pH 8) and stirred at 25° C. until dissolution was complete (10 minutes). PLE was added and the pH was maintained at 8.0 by the addition of 0.01 N NaOH. The rate of acid production was determined from the rate of base addition over a period of 5 minutes.

Enzyme stability was measured while the reaction was in progress. Measurements were performed by periodically removing aliquots of the enzyme solution and determining the activity using the ethyl butyrate assay.

Example 2

CLEC™-PLE Catalyzed Reaction of FTC Butyrate in 83% of n-amyl Alcohol (or 3-Me-3-pentanol)/Aqueous Mixture The reaction conditions and procedures were the same as in Example 1, except the volume of phosphate buffer was 1 ml and the volume of the organic component was 8.3 ml. The conversion was 38% for n-amyl alcohol and 25% for 3-methyl-3-pentanol after 36 h (see Table 1, Reactions 12 and 13).

Example 3

PSL-Catalyzed Reaction of FTC Butyrate in 50% n-amyl Alcohol/Aqueous Mixture

The reaction conditions and procedures were the same as in Example 1, except that 100 mg of soluble PSL-30 (PSL-30 is PS30 from Amano) was used. The conversion was 56% after 24 h and the (−)-enantiomer was preferentially hydrolyzed. The optical purity of the remaining ester was 92% at 56% conversion (see Table 1, Reaction 21).

Example 4

ANL-Catalyzed Reaction of FTC Butyrate in 50% n-amyl Alcohol/Aqueous Mixture

The reaction conditions and procedures were the same as in Example 1, except that 200 mg of soluble ANL was used. The conversion was 45% after 36 h. The optical purity of the remaining ester was 63% at 45% conversion (see Table 1, Reaction 22).

Example 5

PLE-Catalyzed Conversion of (+)-FTC Butyrate in 20% of isopropanol (or Other Water-Miscible Organic Co-Solvents)/Aqueous Mixture with 2% Substrate Concentration The following example illustrates the state of the art using high amounts of enzyme catalysts in a of homogeneous system. To a solution of 1 ml of Altus PLE solution 650 units/ml from Altus Biologics, Inc. in 39 ml of 0.3 M phosphate buffer (pH 7.5) was added 10 ml of 10% FTC butyrate in isopropanol. The resulting mixture was stirred 24~26° C. and the reaction progress was monitored by HPLC. The conversion reached 51% and the optical purity of the remaining chiral nonracemic ester compound was greater than 99% (48% chemical yield) after a 22 h reaction. These results are based on HPLC analysis of the remaining chiral nonracemic ester compound. The aqueous layer included hydrolyzed products (+)-FTC and (−)-FTC. The ratio of (+)-FTC and (−)-FTC was 96.6 to 3.4. The organic layer was evaporated to give 0.457 g of (−)-FTC butyrate.

A similar reaction was performed by using other water miscible organic co-solvents, including acetonitrile, DMF, 1-methyl-2-pyrrolidinone, methanol, ethanol, tert-butanol, DMSO, pyridine, di(ethylene glycol)methyl ether, PEG 200, and PEG 600 etc. Acetonitrile gave the same high enantioselectivity as isopropanol and required similarly large amounts of enzyme. All other solvents gave lower enantioselectivity than isopropanol.

Example 6

PLE-Catalyzed Conversion of (±)-FTC Butyrate in 20% of Isopropanol/Aqueous Mixture with 5% Substrate Concentration To a solution of 2.5 ml of Altus PLE solution 650 units/ml from Altus Biologics, Inc. in 37.5 ml of 0.3 M phosphate buffer (pH 7.5) was added 10.0 ml of 25% FTC butyrate in isopropanol. Under these conditions, the substrate was incompletely dissolved. The resulting mixture was stirred at 24~26° C. and the reaction was monitored by HPLC. The conversion reached 60% and the optical purity of the remaining ester was 74% (38% chemical yield) after 96 h reaction time. The enantioselectivity was much lower than the reaction with a 2% substrate concentration.

Example 7

PLE-Catalyzed Conversion of (±)-FTC Butyrate in 30% Isopropanol/Aqueous Solution and a 3% Substrate Concentration To a solution of 1.5 ml of Altus PLE solution 650 units/ml from Altus Biologics, Inc. in 33.5 ml of 0.3 M phosphate buffer (pH 7.5) was added 15 ml of 10% FTC butyrate in isopropanol. The resulting mixture was stirred at 24~26° C. and the reaction was monitored by HPLC. The conversion was 8% after 2 h and did not increase after that. The enzyme rapidly lost all activity in the 30% isopropanol.

Table 1 summarizes the results of resolution reactions of FTC-butyrate with various enzymes in biphasic non-homogeneous systems comprising various not more than about 50% water miscible organic solvents and aqueous buffer solutions.

TABLE 1

Resolution of an enantiomeric mixture of FTC-butyrate with various enzymes in various biphasic systems[a]

| Rxn | enzyme | co-organic solvent | time (h) | conversion (%) | ee (%)[b] ester | stereochem. preference |
|---|---|---|---|---|---|---|
| 1 | PLE-C[c] | n-amyl alcohol | 24 | 52 | >98 | (+) |
| 2 | PLE-I[c] | n-amyl alcohol | 36 | 53 | >98 | (+) |
| 3 | PLE-S[c] | n-amyl alcohol | 24 | 52 | >98 | (+) |
| 4 | PLE-C | iso-amyl alcohol | 36 | 52 | >98 | (+) |
| 5 | PLE-C | tert-amyl alcohol | 36 | 37 | 59 | (+) |
| 6 | PLE-C | 1-butanol | 24 | 12 | 10 | (+) |
| 7 | PLE-C | 2-butanol | 24 | 7 | 7.5 | (+) |
| 8 | PLE-C | 3-pentanol | 36 | 40 | 67 | (+) |
| 9 | PLE-C | 1-heptanol | 36 | 39 | 64 | (+) |
| 10 | PLE-C | 3-heptanol | 36 | 39 | 52 | (+) |
| 11 | PLE-C | 3-Me-3-pentanol | 36 | 53 | >98 | (+) |
| 12 | PLE-C | 3-Me-3-pentanol[d] | 36 | 25 | 33 | (+) |
| 13 | PLE-C | n-amyl alcohol[d] | 36 | 38 | 61 | (+) |
| 14 | PLE-C | 4-Me-2-pentanol | 36 | 45 | 82 | (+) |
| 15 | PLE-C | 3-Et-3-pentanol | 36 | 48 | 92 | (+) |
| 16 | PLE-C | nitromethane | 36 | 24 | 32 | (+) |
| 17 | PLE-C | dichloromethane | 36 | 20 | 25 | (+) |
| 18 | PLE-C | toluene | 36 | 18 | 16 | (+) |
| 19 | PLE-C | methyl isobutyl ketone | 36 | 20 | 33 | (+) |
| 20 | PLE-C | tert-butyl acetate | 36 | 23 | 29 | (+) |
| 21 | PSL | n-amyl alcohol | 24 | 56 | 92 | (−) |
| 22 | ANL | n-amyl alcohol | 36 | 45 | 63 | (+) |

[a]Reaction conditions: 1 g of (±) FTC-butyrate in 10 ml of 50% organic/aqueous mixture was hydrolyzed with PLE, PSL or ANL at room temperature.
[b]The optical purity was based on HPLC analysis.
[c]PLE-C = CLEC ™-PLE, PLE-I = immobilized PLE, PLE-S = Altus PLE solution 650 units/ml.
[d]in 6 ml or 83% organic/aqueous mixture.

Examples 5-7 illustrate some of the problems with using water miscible alcohols in homogeneous systems for the process of the present invention. Such systems produce product with reduced optical purity, prolong reaction times, and deactivate the enzyme.

Examples 8-13
PLE Catalyzed Conversion of (+) FTC-Butyrate in Non-Homogeneous Systems Using n-Amyl Alcohol and Water The reaction conditions and procedures were the same as in Example 1. The non-homogeneous system comprises 1 ml of Altus PLE solution (650 U/ml) as catalyst and the volumes of amyl alcohol and phosphate buffer used are indicated in Table 2 below. Note that in each case, the selectivity of conversion of the (+)-isomer was almost absolute, so that the desired conversion of slightly greater than 50% results in enantiomeric purities of the unreacted (−) ester of nearly 100% (See Table 2).

TABLE 2

Examples 8 through 13

| | Example | | | | | |
|---|---|---|---|---|---|---|
| | 8 | 9 | 10 | 11 | 12 | 13 |
| Amyl Alcohol | 2 ml | 3 ml | 4 ml | 5 ml | 6 ml | 7 ml |
| Phosphate buffer | 7 ml | 6 ml | 5 ml | 4 ml | 3 ml | 2 ml |

TABLE 2-continued

Examples 8 through 13

| Reaction time (h) | % Conversion | | | | | |
|---|---|---|---|---|---|---|
| 0 | 0 | 0 | 0 | 0 | 0 | 0 |
| 1 | 28 | 26 | 24 | 21 | 20 | 19 |
| 3 | 43.2 | 42 | 39 | 34 | 33 | 33 |
| 8 | 49 | 49 | 48 | 45 | 41 | 41 |
| 24 | 49.8 | 49.8 | 49.2 | 47.5 | 46.7 | 47.3 |

Examples 14-30

PLE-Catalyzed Conversion of (±) FTC-Butyrate in Non-Homogeneous Systems Comprising n-amyl Alcohol and Water Mixtures in the Presence of Surfactants Examples 14 through 30 are shown in Table 3. The reaction conditions and procedures were the same as in Example 1. The non-homogeneous system comprises 1 ml of Altus PLE solution (650 U/ml) as catalyst and 1 ml (Examples 14-21, 23, 24, and 30) or 0.1 g of surfactant (Examples 25-29) were added as surfactant to the reaction mixtures. The organic component comprised n-amyl alcohol and the aqueous component comprised 0.3 M phosphate buffer in a 50:50 ratio.

TABLE 3

Examples 14 through 30

| Example | Surfactant | % Conversion at time (t) (t) Hours | | | | |
|---|---|---|---|---|---|---|
| | | 0 | 1 | 3 | 7 | 24 |
| 14 | TWEEN ® 20 | 0 | 18 | 34 | 45 | 50 |
| 15 | PRIONEX ® | 0 | 17 | 30 | 42 | 49 |
| 16 | TEEPOL ® HB7 | 0 | 9 | 15 | 21 | 26 |
| 17 | TERGITOL ® TMN-6 | 0 | 14 | 32 | 44 | 48 |
| 18 | TERGITOL ® 15-S-3 | 0 | 17 | 29 | 40 | 47 |
| 19 | IGEPAL ® CA-630 | 0 | 19 | 35 | 45 | 49 |
| 20 | Tyloxapol | 0 | 18 | 35 | 46 | 50 |
| 21 | TERGITOL ® TMN-10 | 0 | 17 | 30 | 42 | 48 |

| Example | Surfactant | % Conversion at time (t) (t) Hours | | | |
|---|---|---|---|---|---|
| | | 0 | 1 | 3 | 20 |
| 22 | No Surfactant | 0 | 21 | 34 | 47.5 |
| 23 | AEROSOL ® 22 | 0 | 7 | 7 | 8 |
| 24 | TERGITOL ® NP-4 | 0 | 18 | 34 | 49.5 |
| 25 | Glucode-oxycholic acid | 0 | 14 | 25 | 44 |
| 26 | Octyl β-gluco-pyranoside | 0 | 15 | 30 | 47 |
| 27 | Chaps | 0 | 14 | 21 | 39 |
| 28 | Dioctyl Sulfosuccinate Na + salt | 0 | 17 | 32 | 49.5 |
| 29 | Deoxy-cholic acid Na + salt | 0 | 13 | 23 | 43.4 |
| 30 | TWEEN ® 80 | 0 | 18 | 33 | 50 |

The broad screening of surfactants, as shown in Table 3, reveals that some are activating (see Examples 14, 15, 19, 20, 24, 28, and 30) and some are inhibitory (see 16, 23, 27 and 29). Fifteen surfactants were chosen for further analysis. The surfactants TERGITOL® NP-4, TWEEN® 80, Tyloxapol and dioctyl sulfosuccinate sodium all enhanced the PLE activity to roughly the same extent. The enhancement in rate is most apparent at the end of the reaction and may be due to stabilization of the enzyme and prevention of precipitation as well as an effect on catalytic efficiency.

Example 31-34

PLE Catalyzed Conversion of (±) FTC-Butyrate in Bi-Phasic n-Amyl Alcohol/Water Mixtures in the Presence of TWEEN®-80

Examples 31 through 34 are shown in Table 4. The reaction conditions and procedures were the same as in Example 1. The non-homogeneous system comprises TWEEN® 80 as surfactant, 0.6 ml Altus PLE solution (650 U/ml) as the catalyst and the volume of amyl alcohol and 0.3 M phosphate buffer used are indicated in the table below.

TABLE 4

Examples 31 through 34

| | Example | | | |
|---|---|---|---|---|
| | 31 | 32 | 33 | 34 |
| Amyl Alcohol | 4 ml | 4.5 ml | 4.75 ml | 4.9 ml |
| TWEEN ®-80 | 1 ml | 0.5 ml | 0.25 ml | 0.1 ml |
| Phosphate buffer 0.3M | 5 ml | 5 ml | 5 ml | 5 ml |
| Reaction time (h) | 1 | 1 | 1 | 1 |
| % Conversion | 10 | 8 | 6 | 5 |

Examples 35
Complimentary Reductions in Both Enzyme and Organic Solvent Requirements The reaction conditions and procedures were the same as in Example 1. The non-homogeneous system comprised 0.5 ml of TWEEN® 80 as surfactant, 0.3 ml of Altus PLE solution (650 U/ml) as catalyst, and 2.0 ml of amyl alcohol and 7.5 ml of 0.3 M phosphate buffer were the solvents. The non-homogeneous system comprised 25% organic component and 75% aqueous component. After 48 hours, the extent of conversion was 50% and the optical purity of the remaining ester was 99.3%.

In this example, the amount of both enzyme and organic solvent were reduced by approximately half from the level used in Examples 31-34, with no loss of product yield. Furthermore, the enzyme requirement was only 25% of that required in Example 1.

Examples 36-39
Dioctyl Sulfosuccinate (Dioctyl SS) as Surfactant

Examples 36 through 39 are shown in Table 5. The reaction conditions and procedures were the same as in Example 1. The non-homogeneous system comprised dioctyl sulfosuccinate (Dioctyl SS) as surfactant and 0.4 ml of Altus PLE enzyme solution (650 U/ml) in 8 ml of 0.3 M phosphate buffer and 2 ml of amyl alcohol.

TABLE 5

Examples 36 through 39

| | Example | | | |
|---|---|---|---|---|
| | 36 | 37 | 38 | 39 |
| Dioctyl SS | 10 mg | 25 mg | 100 mg | 200 mg |
| Time (h) | Conversion | | | |
| 0 | 0 | 0 | 0 | 0 |
| 1 | 5 | 5.5 | 9 | 9 |
| 3 | 20 | 22 | 25 | 23 |
| 5.5 | 27 | 32 | 34 | 30 |
| 21 | 40 | 47 | 48 | 45 |

Example 40

The reaction conditions and procedures were the same as in Example 1. The catalyst comprised 714 total units of porcine liver esterase (Sigma, St. Louis, Mo.). The non-homogeneous system comprised 50% n-amyl alcohol as organic component and 50% 0.3 M phosphate buffer at pH 7.4 as aqueous component. After 24 hours, the extent of conversion was 50% and the optical purity of the remaining ester was 97.5%.

Example 41

Rate Enhancement with Low Enzyme Loadings and Anionic Surfactant

In addition to the use of TWEEN®-80, the anionic surfactant dioctyl sulfosuccinate sodium salt, was chosen to achieve rate enhancement. As shown in Table 6, a 1% loading of this surfactant in the non-homogeneous system was sufficient for significant rate enhancement.

Reaction conditions included: 1 g FTC butyrate, 0.4% PLE loading, organic solvent 1-pentanol, 2:8 solvent ratio, reaction carried out at 30° C. (Table 6).

TABLE 6

Example 41

| Time | % Conversion with (x mg) Surfactant | | | |
|---|---|---|---|---|
| | mg surfactant | | | |
| (h) | 10 mg | 25 mg | 100 mg | 200 mg |
| 0 | 0 | 0 | 0 | 0 |
| 1 | 5 | 5.5 | 9 | 9 |
| 3 | 20 | 22 | 25 | 23 |
| 5.5 | 27 | 32 | 34 | 30 |
| 21 | 40 | 47 | 48 | 45 |

Example 42

Surfactant Effect on Enzyme Loading and Organic Solvent Concentration

A preferred embodiment of this invention includes an enzyme loading of 0.3 to 0.4% relative to FTC butyrate with a 10% substrate loading. A number of reactions were performed on slightly larger scale to more accurately determine the run to run variation and the effect of conversion on optical purity. The results are shown in Table 7 below.

TABLE 7

5 g Scale Reactions at Low Enzyme Loadings
28° C., 45% 1-pentanol, 5% TWEEN ®-80, 50% aqueous)

| PLE (%) | TWEEN ®-80 (%) | Time (h) | Optical Purity (% e.e.) |
| --- | --- | --- | --- |
| 0.6 | 2.5 | 26 | 95.32 |
| 0.6 | 5 | 24 | 98.34 |
| 0.4 | 5 | 24 | 96.20 |
| 0.4 | 5 | 42 | >99.0 |

As show in Table 8, reactions performed at a lower organic/aqueous ratio and with a 0.3% enzyme loading gave high optical purity in less than 48 hours.

TABLE 8

1 g Scale Reaction at Low Enzyme Loadings,
(28° C. in 20% 1-pentanol/5% TWEEN ®-80, 75% aqueous)

| PLE (%) | Time (h) | e.e (%) |
| --- | --- | --- |
| 0.4% | 25 | 99.20 |
| 0.3% | 25 | 95.88 |
| 0.3% | 31 | 97.68 |
| 0.3% | 48 | 99.32 |

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A biphasic, non-homogenous composition for resolving a compound of Formula A:

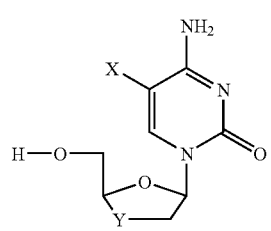

Formula A wherein:
X=F;
Y=S;
comprising:
(a) a hydrolase enzyme;
(b) an enantiomeric mixture of a compound of Formula B:

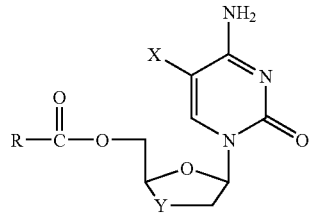

Formula B wherein:
R is $C_1$-$C_8$ alkyl, $C_2$-$C_8$ alkenyl, or $C_2$-$C_8$ alkynyl;
X=F;
Y=S;
(c) an organic component comprising an organic solvent;
(d) an aqueous component in contact with the organic component;
wherein the enantiomeric mixture is dispersed in the organic component at a concentration of between 5% and 45% weight/volume of the non-homogenous composition.

2. The non-homogeneous composition of claim 1, wherein the compound of Formula B is 2-butyryloxymethyl (5-fluorocytosin-yl)-1,3-oxathiolane.

3. The non-homogeneous composition of claim 1, wherein the organic component comprises between about 5 and about 90% of the non-homogeneous composition; and the non-homogeneous composition also comprises between about 1 and about 20% of a surfactant.

4. The non-homogeneous composition of claim 1, wherein the hydrolase enzyme is selected from the group consisting of porcine liver esterase, porcine pancreatic lipase, *Pseudomonas* species lipase, *Aspergillus niger* lipase and subtilisin.

5. The non-homogeneous composition of claim 1, wherein the hydrolase enzyme is a crosslinked enzyme crystal.

6. The non-homogeneous composition of claim 5, wherein the crosslinked enzyme crystal is crosslinked with glutaraldehyde.

7. The non-homogeneous composition of claim 1, wherein the hydrolase enzyme is an immobilized enzyme.

8. The non-homogeneous composition of claim 1, wherein the hydrolase enzyme is a soluble enzyme.

9. The non-homogeneous composition of claim 4, wherein said hydrolase enzyme is porcine liver esterase.

10. The non-homogeneous composition of claim 1, wherein the enantiomeric mixture is dispersed in the organic component to a concentration of between 5% to 20%.

11. The non-homogeneous composition of claim 1, wherein the enantiomeric mixture is dispersed in the organic component to a concentration of between 10% to 30%.

12. The non-homogeneous composition of claim 1, wherein said organic component comprises a not more than 50% water miscible organic solvent.

13. The non-homogeneous composition of claim 12, wherein said not more than 50% water miscible organic solvent comprises one or more solvents selected from the group consisting of $C_4$-$C_8$ alcohols, nitromethane, dichloromethane, toluene, methyl isobutyl ketone, tert-butyl acetate and alkanes.

14. The non-homogeneous composition of claim 13, wherein said organic component comprises one or both of n-amyl alcohol and 3-methyl pentanol.

15. The non-homogeneous composition of claim 3, wherein said surfactant is selected from the group consisting of cationic surfactants, anionic surfactants and non-ionic surfactants.

16. The non-homogeneous system of claim 15, wherein said surfactant is selected from the group consisting of polyoxyethylenesorbitan monolaurate; polyoxyethylenesorbitan monooleate; 10% aqueous solution of a polypeptide fraction of porcine dermal collagen; 2,6,8-trimethyl-4-nonyloxypolyethylenoxyethanol; 2-(2,6,8-trimethylnonan-4-yloxy)ethanol); nonylphenol ethoxylate; secondary alcohol ethoxylate; branched octylphenoxypoly(ethyleneoxy)ethanol; phenol, 4-(1,1,3,3-tetramethylbutyl) polymer with formaldehyde and oxirane; glucode-oxycholic acid; octyl β-gluco-pyranoside; and dioctyl sulfosuccinate sodium salt.

17. The non-homogeneous composition of claim 16, wherein the surfactant is polyoxyethylenesorbitan monooleate.

18. The non-homogeneous composition of claim 16, wherein said surfactant is dioctyl sulfosuccinate sodium salt.

19. The non-homogeneous composition of claim 15, wherein the organic component comprises the surfactant.

20. The non-homogeneous composition of claim 15, wherein the aqueous solvent system comprises the surfactant.

21. The non-homogeneous composition of claim 15, wherein the surfactant is formulated with the hydrolase enzyme.

22. The non-homogeneous composition of claim 1, wherein said aqueous solvent system comprises water and excipients selected from the group consisting of buffering salts, alkalizing agents, anti-microbial preservatives, stabilizers, filtering aids, co-enzymes, excipients that facilitate dispersion and excipients that facilitate function of the enzyme.

23. The non-homogeneous composition of claim 22, wherein said aqueous solvent system comprises water buffered with phosphate buffer at a pH of greater than 7.

24. The non-homogeneous composition of claim 22, wherein said wherein said aqueous solvent system comprises water buffered with 2-amino-2-(hydroxymethyl)-1,3-propanediol or Tris.

25. The non-homogeneous composition of claim 1, wherein the conditions which permit the enantioselective conversion of one enantiomeric form of the enantiomeric mixture to the corresponding alcohol comprise a temperature between about 5° C. and 45° C.

26. The non-homogeneous system of claim 16, wherein said surfactant is selected from the group consisting of polyoxyethylenesorbitan monolaurate; polyoxyethylenesorbitan monooleate; 10% aqueous solution of a polypeptide fraction of porcine dermal collagen; nonylphenol ethoxylate; branched octylphenoxypoly(ethyleneoxy)ethanol; phenol, 4-(1,1,3,3-tetramethylbutyl) polymer with formaldehyde and oxirane; and dioctyl sulfosuccinate sodium salt.

* * * * *